(12) United States Patent
Moses et al.

(10) Patent No.: US 8,153,837 B2
(45) Date of Patent: Apr. 10, 2012

(54) RESORBABLE PHENOLIC POLYMERS

(75) Inventors: Arikha Moses, New York, NY (US);
Satish Pulapura, Bridgewater, NJ (US);
Arthur Schwartz, East Windsor, NJ (US); Qing Ge, Plainsboro, NJ (US);
Irene Shatova, Jamesburg, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 807 days.

(21) Appl. No.: 12/279,539

(22) PCT Filed: Nov. 3, 2006

(86) PCT No.: PCT/US2006/042944
§ 371 (c)(1),
(2), (4) Date: Nov. 24, 2008

(87) PCT Pub. No.: WO2007/056134
PCT Pub. Date: May 18, 2007

(65) Prior Publication Data
US 2009/0088548 A1  Apr. 2, 2009

Related U.S. Application Data

(60) Provisional application No. 60/733,988, filed on Nov. 3, 2005.

(51) Int. Cl.
*C07C 69/00* (2006.01)
*C08G 65/38* (2006.01)
(52) U.S. Cl. ............. 560/39; 560/42; 528/182; 528/210
(58) Field of Classification Search .................. None
See application file for complete search history.

(56) References Cited

U.S. PATENT DOCUMENTS

| | | |
|---|---|---|
| 4,980,449 A | 12/1990 | Kohn et al. |
| 5,099,060 A | 3/1992 | Kohn et al. |
| 5,198,507 A | 3/1993 | Kohn et al. |
| 5,216,115 A | 6/1993 | Kohn et al. |
| 5,587,507 A | 12/1996 | Kohn et al. |
| 5,658,995 A | 8/1997 | Kohn et al. |
| 5,670,602 A | 9/1997 | Kohn et al. |
| 6,048,521 A | 4/2000 | Kohn et al. |
| 6,120,491 A | 9/2000 | Kohn et al. |
| 7,271,234 B2 | 9/2007 | Kohn et al. |
| 2004/0254334 A1 | 12/2004 | James et al. |
| 2006/0115449 A1* | 6/2006 | Pacetti ........................ 424/78.27 |

OTHER PUBLICATIONS

Database CAPLUS on STN, Acc. No. 2006:515331, Pacetti, US 20060115449 A1 (Jun. 1, 2006) (abstract).*
Database CAPLUS on STN, Acc. No. 2001:70823, Ovalle et al., Carbohydrate Research (2001), 330(1), p. 131-139 (abstract).*
Database CAPLUS on STN, Acc. No. 2000:446880, Basso et al., Tetrahedron: Asymmetry (2000), 11(8), p. 1789-1796 (abstract).*
Brocchini et al., 1997, "A Combinatorial Approach for Polymer Design." J. Am. Chem. Soc. 119:4553-4554.
Gutowska et al., 1995, "Heparin release from thermosensitive polymer coatings: in vivo studies," J. Biomed Mater. Res. 29(7):811-821.
Hoffman, 1987, "Applications of thermally reversible polymers and hydrogels in therapeutics and diagnostics," J. Controlled Release 6(1):297-305.
Urry et al., 1993, Mat. Res. Soc. Symp. Proc. 292:253-264.

* cited by examiner

*Primary Examiner* — Brian J Davis
(74) *Attorney, Agent, or Firm* — Lerner, David, Littenberg, Krumholz & Mentlik, LLP

(57) ABSTRACT

The invention provides biocompatible resorbable polymers, comprising monomer units having formula (I), formula (II), formula (III) or formula (IV). The polymers degrade over time when implanted in the body, and are useful as components of implantable medical devices.

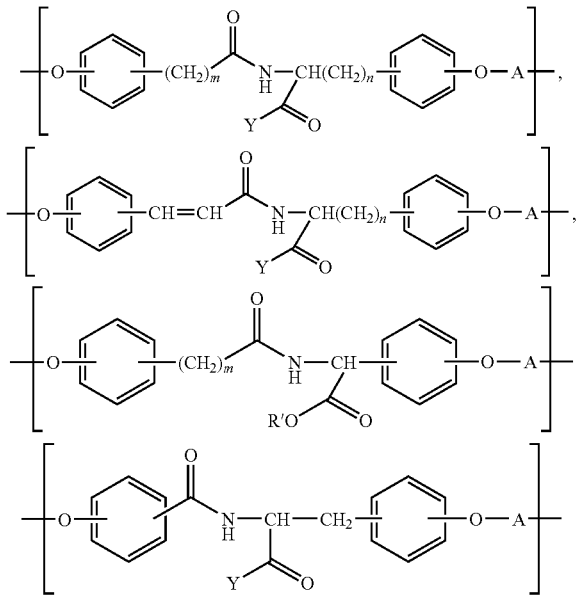

14 Claims, 8 Drawing Sheets

RESORBABLE PHENOLIC POLYMERS

RELATED APPLICATIONS

This application claims priority of U.S. provisional patent application No. 60/733,988, filed Nov. 3, 2005 and incorporated herein by reference.

FIELD OF THE INVENTION

Polymers with specialized properties for medical device coatings are described. These polymers are hydrolytically degradable and resorb within one year. These polymers are derived from monomer units which are relatively water soluble and it is this property that improves the polymers' resorption ability to within 1 year once hydrolytic degradation occurs. The polymers, nonetheless, still provide appropriately robust mechanical properties to function as medical device coatings. The polymers of the invention are based on modifications of the tyrosine-derived family of polyarylates.

BACKGROUND OF THE INVENTION

Diphenols, particularly those derived from tyrosine, are monomeric starting materials for biocompatible polycarbonates, polyiminocarbonates, polyarylates, polyurethanes, and the like. U.S. Pat. Nos. 5,099,060, 5,198,507, and 5,670,602 disclose amino acid-derived diphenol compounds useful in the preparation of polyarylates, polycarbonates and polyiminocarbonates. The polymers, for example those described in U.S. Pat. Nos. 4,980,449, 5,216,115, 5,658,995, 6,048,521, and 6,120,491, and U.S. patent application publication No. 2004/0254334, are useful as degradable polymers in general, and are particularly useful as tissue-compatible bioerodible materials for medical uses. The suitability of these polymers for this end use application is at least in part the result of their derivation from diphenols derived from the naturally-occurring amino acid L-tyrosine.

The polycarbonates in particular are strong, water-insoluble materials most suitable for use as structural implants. The L-tyrosine derived polyarylates described in U.S. Pat. No. 5,216,115, and the poly(alkylene oxide) block copolymers with these polyarylates disclosed in U.S. Pat. No. 5,658,995, feature protected carboxylic acid groups, and these polymers are limited in application because of their slow rate of degradation and significant hydrophobicity. The free acid forms of the polymers, described in U.S. Pat. No. 6,120,491 ("the '491 patent"), in which to varying degrees the ester protecting groups have been removed from the pendent carboxylic acid chains of the diphenols, are less hydrophobic and exhibit an increased degradation rate (i.e. backbone cleavage) compared to their counterparts with fully esterified carboxylic acid groups. Increasing the amount of pendent carboxylic acid diphenol contained within a particular polymer increases the hydrophilicity (water uptake) of the polymer; however, its relative complete resorption rate does not change significantly. This is because the mechanism of degradation—namely, backbone cleavage to successively smaller units containing diphenols with ester protected carboxylic acid groups—does not change the relative water solubility of the esterified monomeric units incorporated within the polymer chains, nor, in the case of the tyrosine-derived polyarylates, does it change the relative water solubility of the diacids with which they are condensed. Therefore, the introduction of an increasing fraction of free carboxylic acid side chains only increases the hydrophilicity of the polymer itself. It does not significantly impact the resorption rate of the ester diphenol fragments produced by polymer backbone degradation.

Hence, medical devices comprised of such materials will retain some significant portion of their mass for roughly the same time period as those polymers described in U.S. Pat. No. 5,099,060, which describes polymers with diphenol monomeric units that lack carboxylic acid side chains. Such polymers resorb completely only in time periods in excess of 1 year, and in many cases in closer to 2-2.5 years. The diphenol monomeric units of these polymers are significantly hydrophobic and have low water solubility.

The '491 patent describes polymers formed from a similar series of diphenol monomeric units but which contain repeating units of the same general diphenol monomers with both protected and unprotected carboxylic acid side chains. The '491 patent teaches that "the incorporation of pendent carboxylic acid groups within the polymer bulk has a dramatic and previously unrecognized accelerating effect on the rate of polymer backbone degradation and resorption both in vitro and in vivo." However, the present inventors have surprisingly found that incorporating some fraction of diphenol monomers with pendant carboxylic acid groups into the polymer does not accelerate overall resorption, because the monomers with protected carboxylic acid groups remain too hydrophobic for resorption on desirable time scales. For example, a polymer incorporating 10% pendant carboxylic acid side chain will degrade (by backbone cleavage) at a faster rate than one containing no pendant carboxylic acid side chains, and some resorption will occur, but this resorption is due to the water solubility of the diphenol monomers containing the pendant carboxylic acid groups. Once this monomer is resorbed, the remaining polymer, albeit one of smaller chain length, contains the protected carboxylic acid side chain monomers which are hydrophobic and resorb at a very slow rate. Incorporating a high fraction of pendant carboxylic acid side chain monomer (e.g., 50% of the diphenol monomer content of the polymer) essentially creates a water-soluble polymer that solubilizes and undergoes degradation until the polymer chain fragments that are enriched in protected pendant carboxylic acid groups precipitate out of solution. The preferred protected monomers in the '491 patent are actually the most hydrophobic and therefore the slowest to resorb, i.e. the ethyl, butyl, hexyl, and octyl esters.

Complete, or nearly complete, polymer resorption (e.g., at least 90%, 95%, 96%. 97%. 98%, 99%, 99.5%, or 100%) is important in the use of "biodegradable" polymers in medical devices. Biodegradable and resorbable polymers are primarily used to deliver drugs for a finite period of time or to serve some other temporary purpose, such as to provide a biocompatible surface, enhanced tissue growth, or extra strength during implantation. Polymers that do not completely resorb leave remnants that can cause anything from minor inflammation and pain to excess scarring, and in the case of cardiovascular implants, such remnants can cause thrombosis and possibly patient death.

SUMMARY OF THE INVENTION

The invention provides polymers with specialized properties, making them particularly suitable for coatings on implanted medical devices, for forming films for use with medical devices, and other uses requiring the short- or defined-term presence of a polymer matrix. The polymers of the invention are hydrolytically degradable and are resorbed by the body within one year. These polymers are derived from monomer units which are relatively water-soluble and it is this property that improves the polymers' resorption time to within 1 year once hydrolytic degradation begins. The polymers nonetheless exhibit sufficiently robust mechanical properties to function as medical device coatings. The polymers of the invention are based on modifications of the tyrosine-derived family of polyarylates.

The need for polymers that resorb within one year (or such lesser times as may be desired), while retaining useful properties (e.g., at least 1 week of drug elution, biocompatibility, and spray coating capability), is met by the present invention. It has now been found that it is possible to effect better resorption by increasing the water solubility of one or more of the component parts of the diphenol or diacid monomer units of the polymer. Thus, the present invention makes it possible to modulate the rate of resorption without compromising the drug release rate or other physical properties optimized for the end use application, by choosing components having increased water solubility and/or or increased hydrolysis rates in vivo. Certain polymers of the invention can, for example, release a drug over at least a 5 day period.

The present invention also makes it possible to create resorbable polymers with pendant carboxylic acid groups, which modulates the hydrophilicity of the polymer as well as the time over which the polymer properties remain intact. This provides a wide variety of drug release capabilities, so that the polymer can be adapted for hydrophobic and hydrophilic drugs. This is a significant improvement over conventional medical polymers such as poly(lactic acid), poly(glycolic acid), polycaprolactone, and the phenolic polyarylates and polycarbonates exemplified in U.S. Pat. No. 6,120,491. This invention allows independent optimization of the useful properties of the polymers, and significantly improves upon the versatility and utility of the phenolic polymer systems known in the art, particularly phenolic polycarbonates, polyarylates, and poly(iminocarbonates), and poly(alkylene oxide) copolymers thereof.

The polymers of the present invention have many uses and may be formed into a variety of products, including but not limited to implantable medical devices with desired lifetimes of less than one year (e.g., adhesion barriers and surgical meshes to aid wound healing), incorporation into implantable medical devices, and combination with a quantity of a biologically or pharmaceutically active compound sufficient for effective site-specific or systemic drug delivery. See, for example, Gutowska et al., *J. Biomater. Res.*, 29, 811-21 (1995) and Hoffman, *J. Controlled Release*, 6, 297-305 (1987). A biologically or pharmaceutically active compound may be physically admixed with, embedded in or dispersed in a polymer of the invention, or the polymer may be applied as an overcoating of another polymer-containing drug layer, where such overcoating delays or slows drug release. In other uses and products, the polymer is in the form of a sheet or a coating applied to an implantable medical device, such as a hernia repair mesh, a stent, or a barrier layer for the prevention of surgical adhesions (see, e.g., Urry et al., *Mat. Res. Soc. Symp. Proc.*, 292, 253-64 (1993).

Another aspect of the present invention provides a method for site-specific or systemic drug delivery, by implanting in the body of a patient in need thereof an implantable drug delivery device containing a therapeutically effective amount of a biologically or pharmaceutically active compound, in a matrix of (or coated with) a polymer of the present invention. Yet another aspect of the present invention provides a method for preventing the formation of adhesions between injured or surgically repaired tissues, by inserting as a barrier between the injured tissues a sheet or coating comprising a polymer of the present invention.

DETAILED DESCRIPTION OF THE INVENTION

Figure 1:
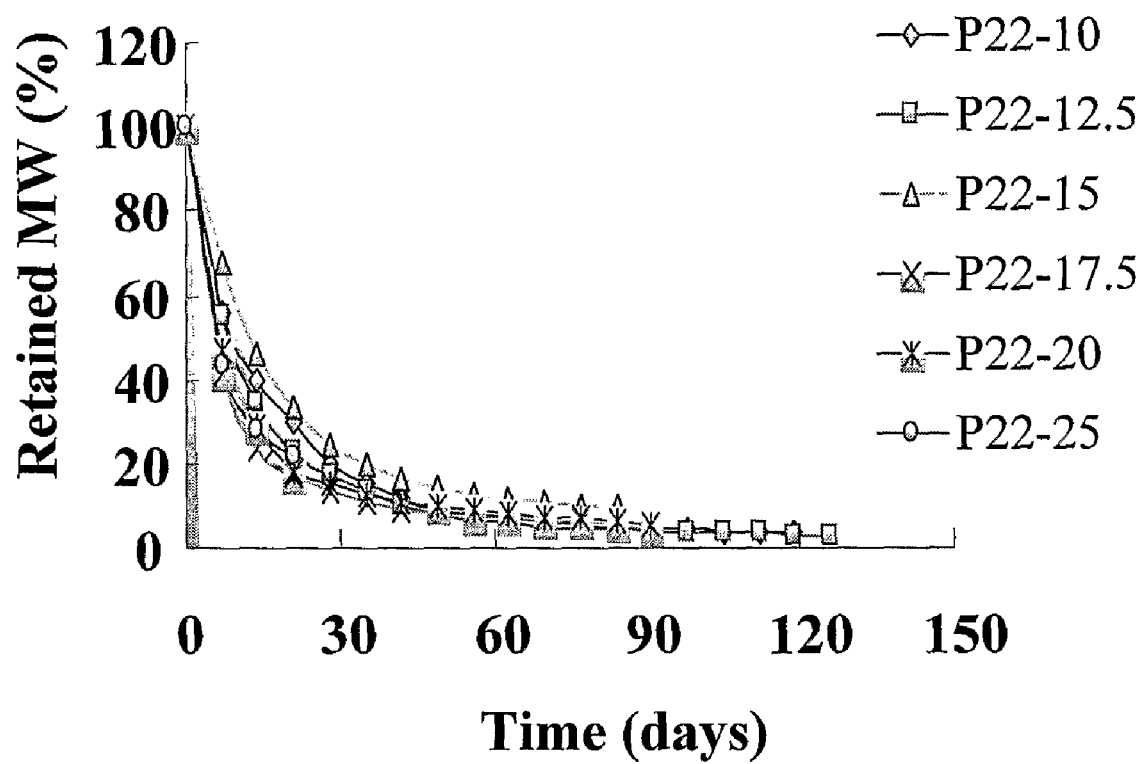
FIG. 1 shows the degradation over time of polymers of the invention.

As used herein, DTE refers to the diphenol monomer desaminotyrosyl-tyrosine ethyl ester; DTBn is the diphenol monomer desaminotyrosyl-tyrosine benzyl ester; DT is the diphenol monomer desaminotyrosyl-tyrosine with a free carboxylic acid. Other diphenol monomers can be named using a similar system. P22 is a polymer produced by condensation of DTE and succinic acid. P22-10, P22-15, P22-20, etc., represent polymers produced by condensation of a mixture of DTE and the indicated percentage of DT (i.e., 10, 15 and 20% DT) with succinic acid. See U.S. patent application publication No. 2004/0254334 for further explanation and examples of the nomenclature of these phenolic polymers.

The invention provides diphenol monomer units having structure

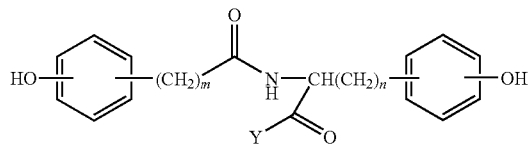

wherein m is 0, 1, or 2; n is 0 to 4, and Y is selected from the group consisting of $C_1$-$C_{18}$ alkylamino, —$NHCH_2CO_2R'$, —$NH(CH_2)_qOR'$, —$NH(CH_2CH_2O)_pR'$, —$NH(CH_2CH_2CH_2O)_pR'$,

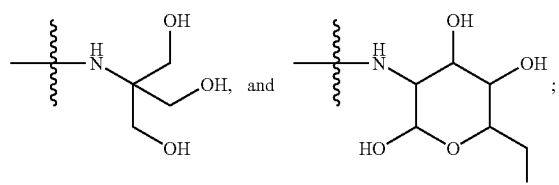

where q is 0 to 4, p is 1 to 5000, and R' is selected from the group consisting of H, $C_1$-$C_8$ alkyl, $C_2$-$C_8$ alkenyl, $C_8$-$C_{14}$ alkylaryl, benzyl, and substituted benzyl. As used herein, the terms alkyl and alkenyl refer to branched- or straight-chain alkyl and alkenyl groups. The term aryl refers to phenyl and naphthyl groups which may be substituted or unsubstituted with halogen, methoxy, alkyl, and the like. The term alkylaryl does not refer to aryl groups having alkyl substituents; it refers to alkyl groups having an aryl substituent. Substituted benzyl refers to benzyl groups substituted with one or more halogens, methoxy groups, nitro groups, alkyl groups, and the like. Substituted benzyl groups known in the art to be suitable for use as protecting groups for ethers and esters are included, including but not limited to 4-methoxybenzyl, 2-methoxybenzyl, 2,4-dimethoxybenzyl, and 2-nitrobenzyl groups.

The invention also provides diphenol monomer units having structure

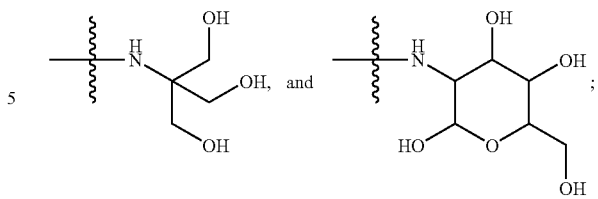

where q is 0 to 4, p is 1-5000 and R' is selected from the group consisting of H, $C_1$-$C_8$ alkyl, $C_2$-$C_8$ alkenyl, $C_8$-$C_{14}$ alkylaryl, benzyl, and substituted benzyl. In preferred embodiments, Y is $NHCH_2CO_2R'$.

The invention also provides diphenol monomer units having structure

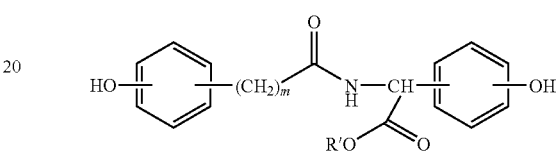

wherein m is 0, 1, or 2; and R' is selected from the group consisting of H, $C_1$-$C_{18}$ alkyl, $C_2$-$C_{18}$ alkenyl, $C_8$-$C_{18}$ alkylaryl, benzyl, and substituted benzyl.

Through co-polymerization of the diphenol monomer units described above with phosgene, cyanogen bromide, or an appropriate diacid, by methods known in the art, the invention provides polymers comprising monomer units having formula

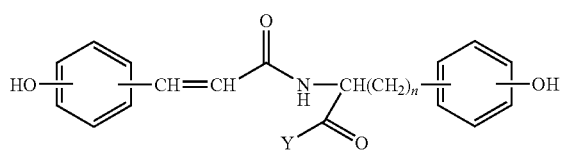

wherein n is 0 to 4; and Y is selected from the group consisting of $C_1$-$C_{18}$ alkylamino, —$NHCH_2CO_2R'$, —$NH(CH_2)_qOR'$, —$NH(CH_2CH_2O)_pR'$, —$NH(CH_2CH_2CH_2O)_pR'$,

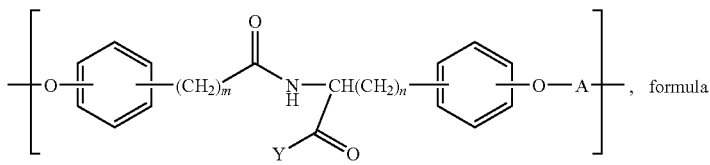, formula

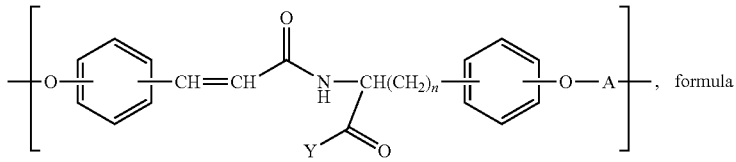, formula

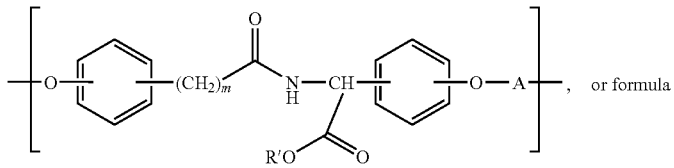, or formula

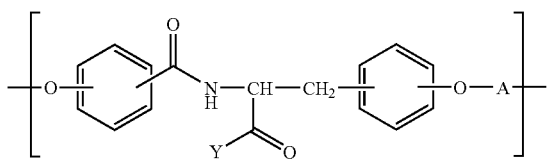

wherein Y is OMe or OEt. In these polymers, m, n, and Y and R' are as defined above, and A is selected from the group consisting of —CO—, —C(=NH)—, and —CO—X—CO—. In these polymers, X is selected from the group consisting of $C_1$-$C_{18}$ alkylene, $C_1$-$C_{18}$ alkenylene, divalent $C_6$-$C_{10}$ arylene, divalent $C_7$-$C_{18}$ alkylaryl, $CH_2OCH_2$, $CH_2O(CH_2CH_2O)_sCH_2$, $(CH_2)_rCO_2(CH_2CH_2CH_2O)_sCO(CH_2)_r$, and $(CH_2)_rCO_2(CH_2CH_2O)_sCO(CH_2)_r$, where r is 2 to 4 and s is 1 to 5000. In specific embodiments of the polymers of the invention, Y is preferably $NHCH_2CO_2R'$.

In certain embodiments, the polymers of the invention consist essentially of monomer units having formula

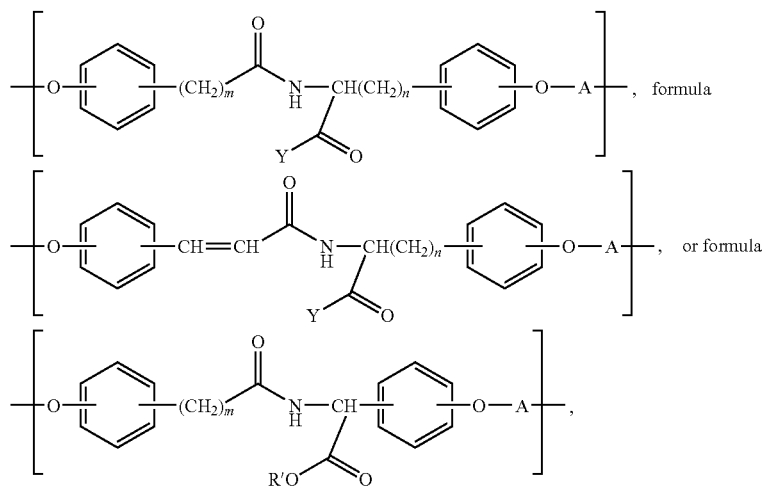

where m, n, A and Y are as defined above.

In certain embodiments, the polymers of the invention as described above further comprising monomer units independently having formula

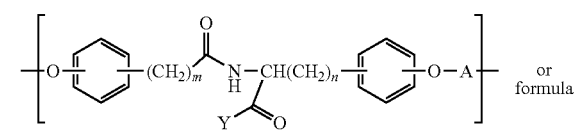

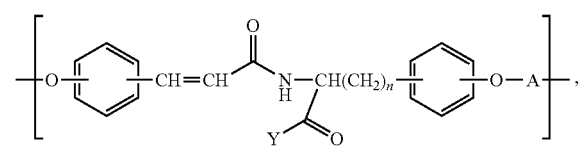

wherein m, n, and A are as defined in claim 5, and Y is OH or O-benzyl.

In preferred embodiments of these polymers, A is —CO—X—CO—, and between 0.1% and 99.9% of the X moieties are $(CH_2)_rCO_2(CH_2CH_2O)_sCO(CH_2)_r$ and/or $(CH_2)_rCO_2(CH_2CH_2CH_2O)_sCO(CH_2)_r$. The range is preferably from about 1% to about 99%, more preferably from about 10% to about 80%. Most preferably, from about 20% to about 50% of the X moieties are $(CH_2)_rCO_2(CH_2CH_2O)_sCO(CH_2)_r$ and/or $(CH_2)_rCO_2(CH_2CH_2CH_2O)_sCO(CH_2)_r$.

In certain preferred embodiments, between about 1% and 50% of the monomer units have formula

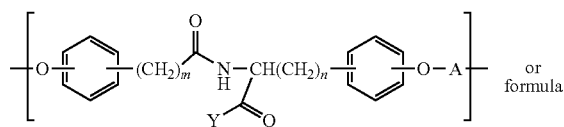

-continued

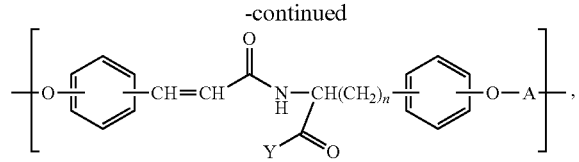

wherein Y is OH or O-benzyl. The range is more preferably from about 5% to about 40%, and most preferably from about 10% to about 30%.

Particularly preferred are polymers wherein A is —CO—X—CO— and X is $CH_2$—O—$(CH_2CH_2O)SCH_2$, with s being 0 to 200. Also provided are polymers comprising monomer units having formula

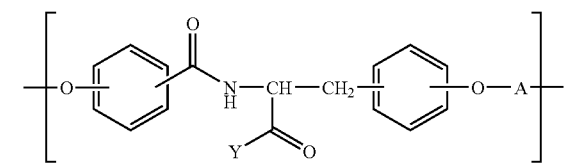

wherein Y is OMe or OEt, A is selected from the group consisting of —CO—, —C(=NH)—, and —CO—X—CO—, and X is selected from the group consisting of $CH_2CH_2$, $CH_2CH_2CH_2$, and $CH_2$—O—$(CH_2CH_2O)_sCH_2$, and s is 0 to 200.

Polymers of the present invention may be formed by reaction of the diphenol monomer units of the invention with a diacid or with phosgene, thereby forming polyarylates and polycarbonates respectively. A schematic diagram of the reaction of the diphenol monomer DTE with a diacid is shown in Scheme 1 below.

The starting moieties are as follows: position 1, tyrosine (T); position 2, desaminotyrosine (D), position 3, ethyl ester (E); position 4, succinate (S or succinate). It is convenient to name the polymer families according to the four positions so

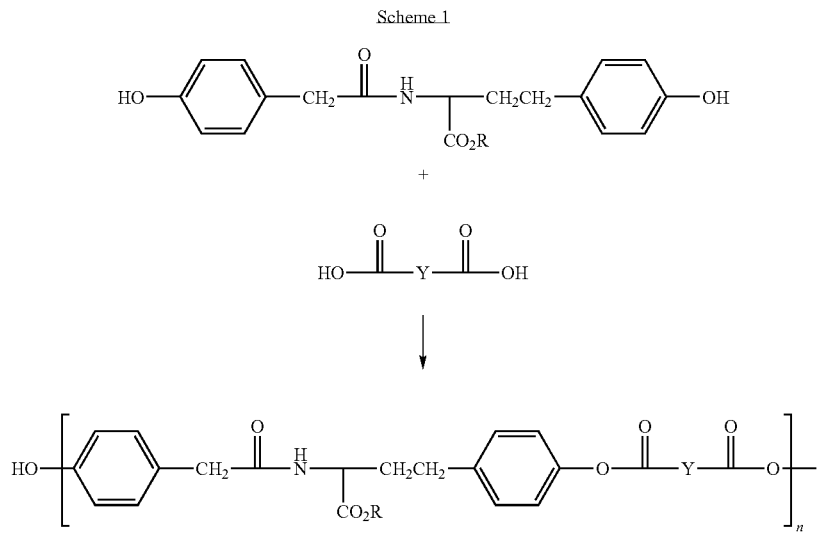

The compounds of the invention are those where the "starting" moieties designated as positions 1-4 below are replaced by one or more moieties that are more hydrophilic or more water-soluble, as illustrated in Tables 1 and 2 below.

that the "starting polymer" with no changes of moieties is DTES or DTE succinate (note this is distinct from DTE, when DTE refers to the diphenol monomeric unit). Either single letters or moiety names are used. Hence examples of polymer

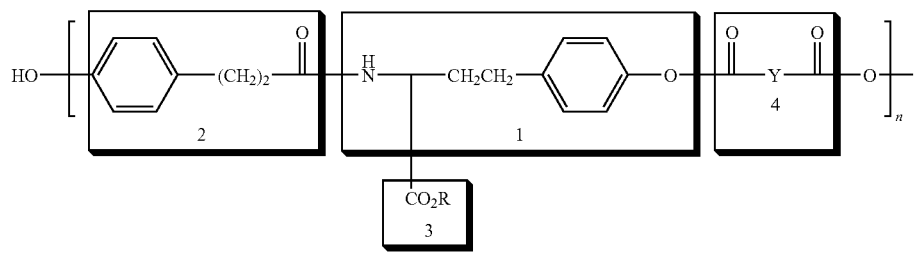

The polymers of the invention thus have at least one of any one of positions 1-4 changed, but can also have 2 positions, 3 positions or all four positions changed. Any permutation of changes to the 4 positions is contemplated, provided that at least one change is made and that at least one change to a moiety make it more soluble than its corresponding starting moiety. In the case of the ester position (position 3), the change may introduce a better leaving group than ethanol. Hence, in accordance with the invention, at least one moiety at one of the positions is more water soluble than its starting moiety; at position 3 the moiety may also be a better leaving group than ethanol, or otherwise be more sensitive to hydrolysis under the conditions of use. By way of example, amides can be more sensitive to hydrolysis in vivo than ethyl esters, due to the action of proteases.

families include BTE glutarate, DTM glutarate, DTM succinate and the like. The single letters for each moiety as used herein are shown in Tables 1 and 2. In Table 1, the bold T is used as a shorthand to represent the remainder of the molecule.

The preferred polymer families of the invention are provided in Table 3 below and do not include all the possible permutations that occur from combining the all four positions. However, all such permutations are contemplated by the invention.

The polymers of the present invention preferably have from 0.1 to 99.9% diphenol monomer DT or from 0.1 to 99.9% PEG diacid to promote the degradation process. The use of either or both methods, i.e. incorporation of DT and/or a PEG diacid (see examples in table below), is within the scope of the invention, and can be used with any of the polymer families of the invention.

TABLE 1
| Chemical Name (Abbrev for polymer family) | DTE Succinate Site Change | water solubility | |
|---|---|---|---|
| Ethyl ester (E) | Site 3: none | | 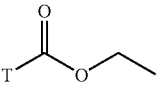 |
| Methyl ester (M) | 3 | | 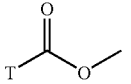 |
| Propyl amide | 3 | | 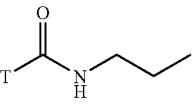 |
| Glycine amide methyl ester | 3 | | 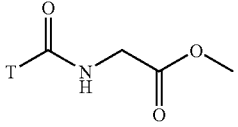 |
| 2-methoxyethyl amide | 3 | | 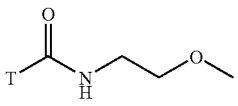 |
| 3-methoxypropyl amide | 3 | | 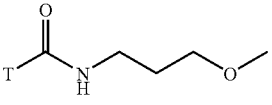 |
| Glycine amide benzyl ester | 3 | | 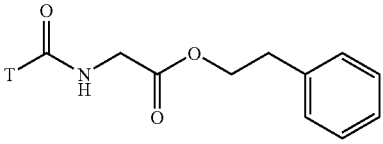 |
| Glycine amide | 3 | | 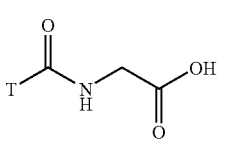 |
| Glucosamine amide | 3 | | |
| PEG amide (n = 1-5000) | 3 | | |
| PEG ester (n = 1-5000) | 3 | | |

TABLE 1-continued

| Chemical Name (Abbrev for polymer family) | DTE Succinate Site Change | water solubility | |
|---|---|---|---|
| Tyrosine (T) | Site 1: none | 0.45 mg/mL | 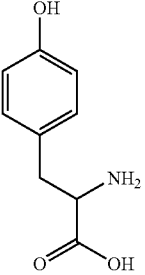 |
| Hydroxyphenyl glycine | 1 | 5 | 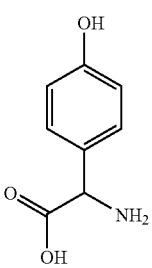 |

TABLE 2

| Basic Elements | Polymer Site Change | Water Solubility | Solubility Difference | |
|---|---|---|---|---|
| Succinic acid | 0 | 76 | 0 | 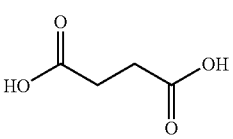 |
| Glutaric acid | 4 | 640 | 9 | 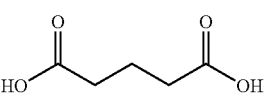 |
| PEG diacid at .01-99% (succinate PEG, n = 1-500) | 4 | Water soluble | Greater than 8; depends on amount of PEG incorporated in backbone | 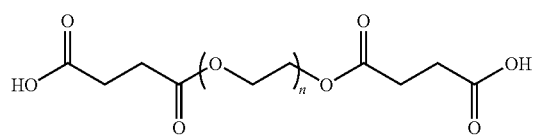 |
| Diglycolic acid | 4 | Water soluble | Greater than 10 | 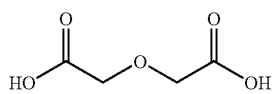 |
| bis(carboxymethyl) PEG (N = 250-600) | 4 | Water soluble | Greater than 10 | 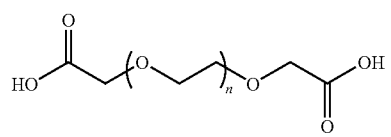 |

TABLE 2-continued
| Basic Elements | Polymer Site Change | Water Solubility | Solubility Difference | |
|---|---|---|---|---|
| DAT | 0 | 1.63 | | 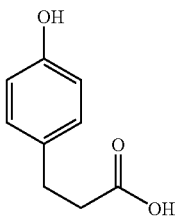 |
| 4-hydroxy benzoic acid | 2 | 8 | 4 | 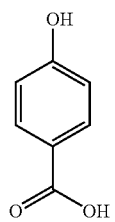 |
| 4-hydroxy phenylacetic acid | 2 | | | 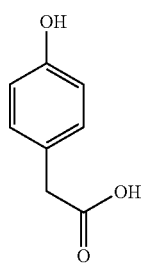 |
| 3-hydroxy benzoic acid | 2 | | | 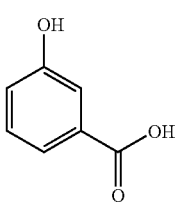 |
| Salicylic acid | | | | |
TABLE 3
| Polymer Family (includes all free acid versions) | |
|---|---|
| BTE glutarate | 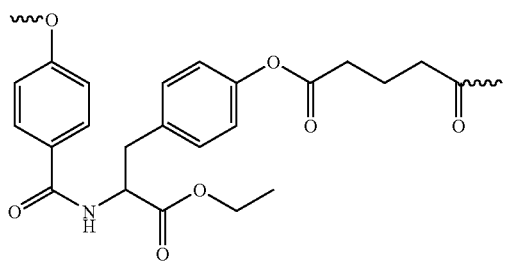 |

TABLE 3-continued
Polymer Family
(includes all free
acid versions)
DTM glutarate
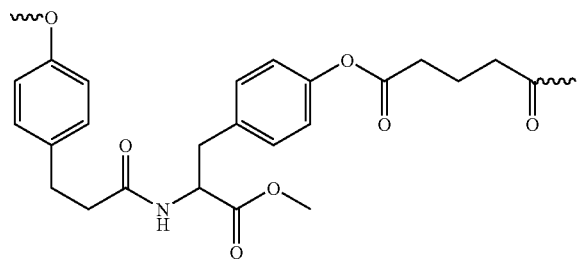
DT Propylamide glutarate
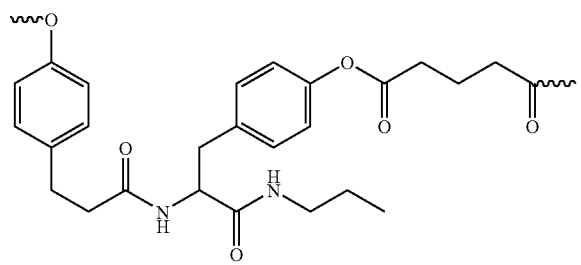
DT Glycinamide methyl ester glutarate
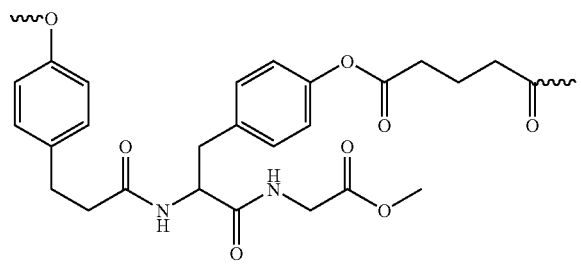
BTE succinate
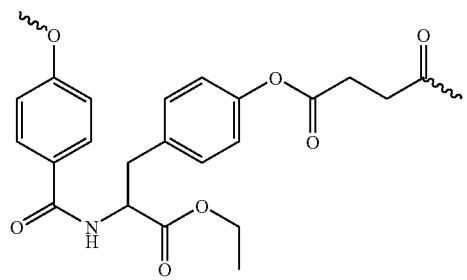
BTM succinate
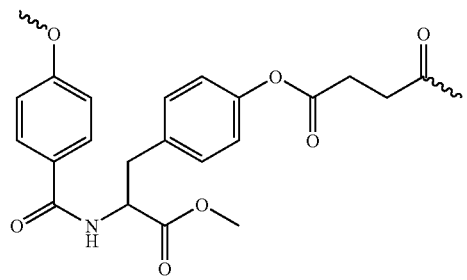

TABLE 3-continued
| Polymer Family (includes all free acid versions) | |
|---|---|
| BTM succinate PEG | 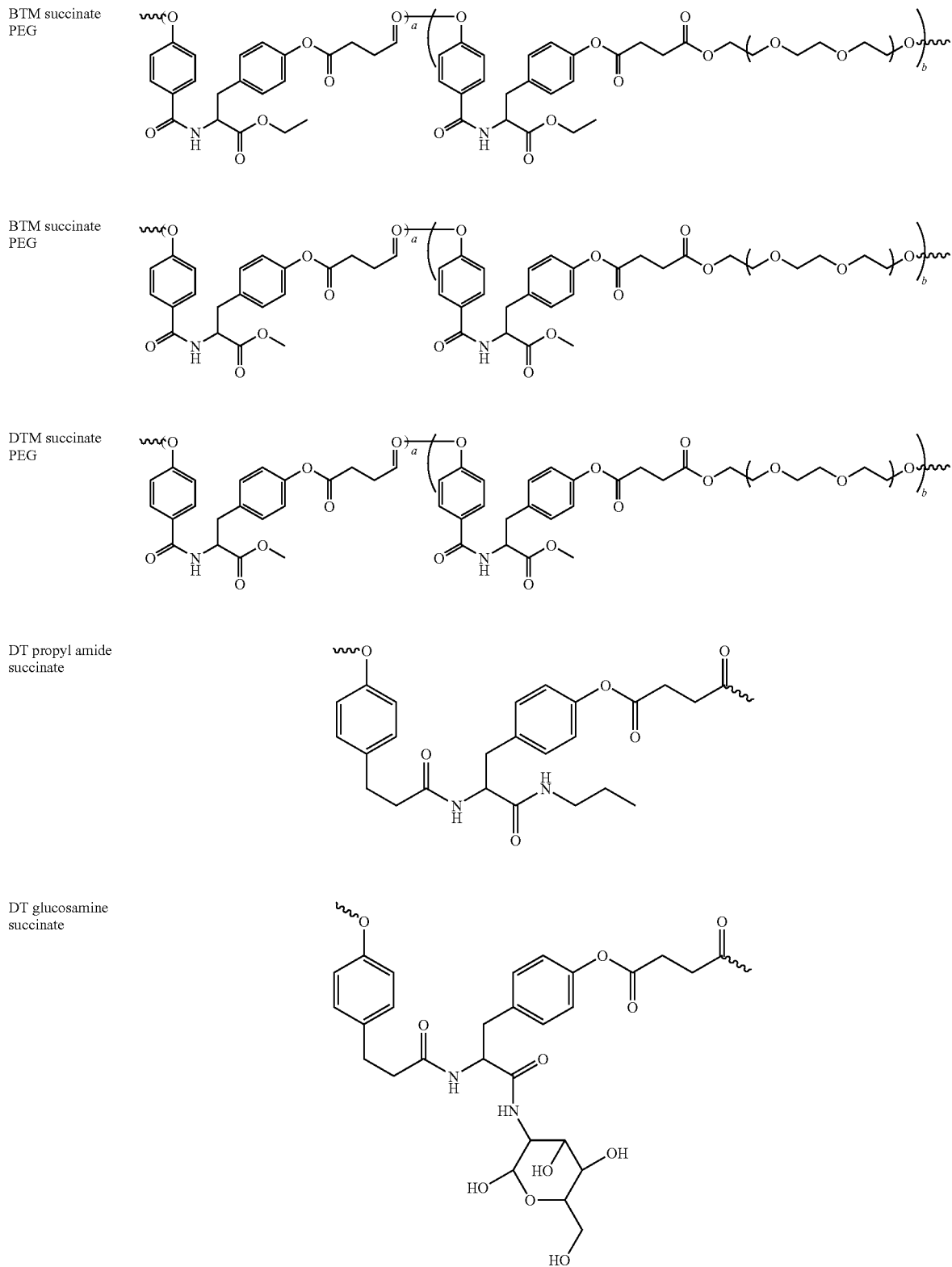 |
| BTM succinate PEG | |
| DTM succinate PEG | |
| DT propyl amide succinate | |
| DT glucosamine succinate | |

TABLE 3-continued
| Polymer Family (includes all free acid versions) | |
|---|---|
| DT glucosamine glutarate | 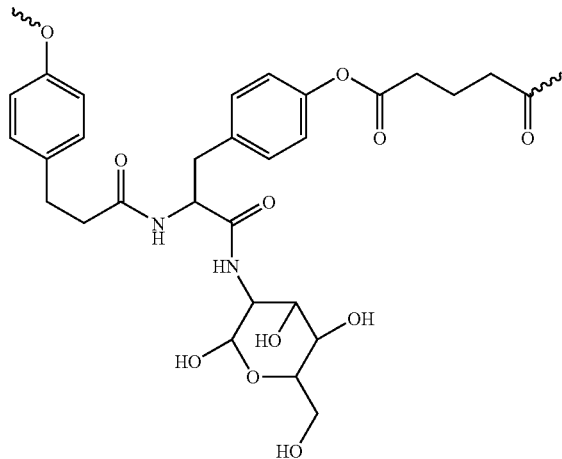 |
| DT PEG amide succinate | 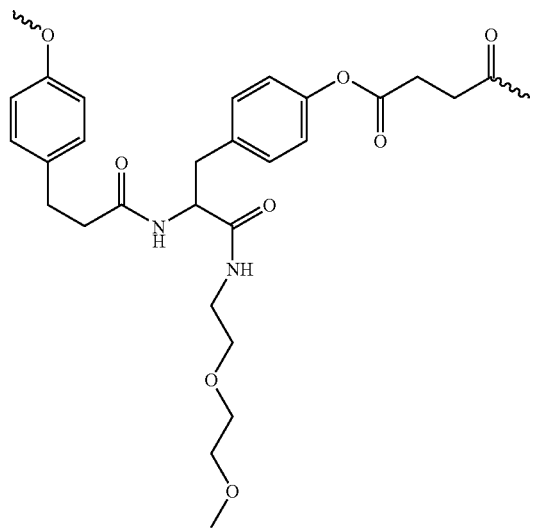 |
| DT PEG amide glutarate | 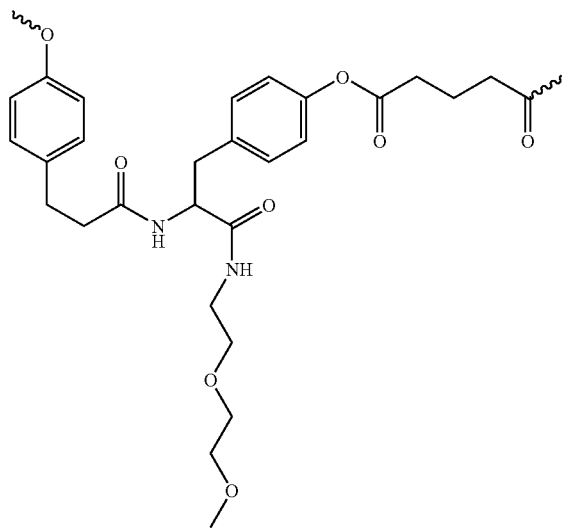 |

Methods for preparing the diphenol monomers are known in the art, for example as disclosed in U.S. Pat. Nos. 5,587,507 and 5,670,602. Methods for preparing polymers with DT content are disclosed in U.S. application publication 2004/0254334.

The polymers of the present invention having pendent carboxylic acid groups may be prepared by the palladium-catalyzed hydrogenolysis of corresponding polymers having pendant benzyl carboxylate groups as describe in the '491 patent. Any other method that allows for the selective deprotection of a pendant carboxylate group is suitable for use in the preparation of the carboxylate-containing polymers of the present invention.

The polymers of the present invention can find application in areas where both solid materials and solvent-soluble materials are commonly employed. Such application include polymeric scaffolds in tissue engineering applications and medical implant applications, including the use of the polycarbonates and polyarylates of the present invention to form shaped articles such as vascular grafts and stents, drug eluting stents, bone plates, sutures, implantable sensors, barriers for surgical adhesion prevention, implantable drug delivery devices, scaffolds for tissue regeneration, and other therapeutic agent articles that decompose harmlessly within a known period of time.

Controlled drug delivery systems may be prepared, in which a biologically or pharmaceutically active agent is physically embedded or dispersed within a polymeric matrix or physically admixed with a polycarbonate or polyarylate of the present invention, or it could be covalently attached to the pendant carboxylic acid.

Examples of biologically or pharmaceutically active compounds suitable for use with the present invention include non-steroidal anti-inflammatories such as naproxen, ketoprofen, ibuprofen; anesthetics such as licodaine, bupivacaine, and mepivacaine; paclitaxel, 5-fluorouracil; antimicrobials such as triclosan, chlorhexidine, rifampin, minocycline; keflex; acyclovir, cephradine, malphalen, procaine, ephedrine, adriamycin, daunomycin, plumbagin, atropine, quinine, digoxin, quinidine, biologically active peptides, chlorin e6, cephradine, cephalothin, cis-hydroxy-L-proline, melphalan, penicillin V, aspirin, nicotinic acid, chemodeoxycholic acid, chlorambucil, and the like. The compounds are covalently bonded to the polycarbonate or polyarylate copolymer by methods well understood by those of ordinary skill in the art. Drug delivery compounds may also be formed by physically blending the biologically or pharmaceutically active compound to be delivered with the polymers of the present invention having pendent carboxylic acid groups, using conventional techniques well-known to those of ordinary skill in the art.

Detailed chemical procedures for the attachment of various drugs and ligands to polymer bound free carboxylic acid groups have been described in the literature. See, for example, Nathan et al., *Bio. Cong. Chem.*, 4, 54-62 (1993).

Biologically active compounds, for purposes of the present invention, are additionally defined as including cell attachment mediators, biologically active ligands and the like.

Processability of the polymers is generally as described in the '491 patent.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

Experimental

Degradation Study Protocol

Molecular weight (MW) profile: For monitoring MW decrease as a function of time, polymer films, or meshes coated with polymer, with approximate dimensions 1×1×0.01 cm, were incubated with 0.01 M PBS or 0.01M PBS with Tween20 (50 to 100 mL) at 37° C. without shaking. At each time point, polymer samples were dissolved in 5 mL of DMF containing 0.1% TFA. The solutions were filtered through 0.45µ Teflon™ syringe-mountable tilters and transferred to analysis vials for analysis by gel permeation chromatography (GPC).

Mass loss profile: For mass loss analysis, films or meshes coated with polymer were incubated with 0.01 M PBS or 0.01M PBS with Tween20 (50 to 100 mL) at 37° C. The buffer in the vials was changed at periodic intervals and analyzed for soluble degrading components. At each time point, 1-2 mL buffer from three small vials was filtered through 0.45µ Teflon™ syringe-mountable filters and transferred to analysis vials for analysis by reversed phase HPLC. Alternately, the devices were washed, dried and weighed (final weight) and the mass loss determined by subtracting the final weight from the original weight.

Polymer Synthesis

DTE (17.85 g), diglycolic acid (6.7 g) and DPTS catalyst (5.88 g) were added to 75 mL methylene chloride. After stirring for 30 minutes, diisopropylcarbodiimide (20 g) was added and the mixture stirred for 24 hours. The polymer formed was isolated by precipitation into 2-propanol. The polymer was purified by three precipitations from methylene chloride/isopropanol to produce the polymer P(DTE diglycolate) in about 65% yield. MW=40 to 75000.

Results

FIG. 1 shows molecular weight (MW) retention as a function of time for various members of the DTE succinate family with DT content ranging from 10-25% of the diphenol content. Very little difference in the degradation times (backbone cleavage) is evident.

Figure 2:
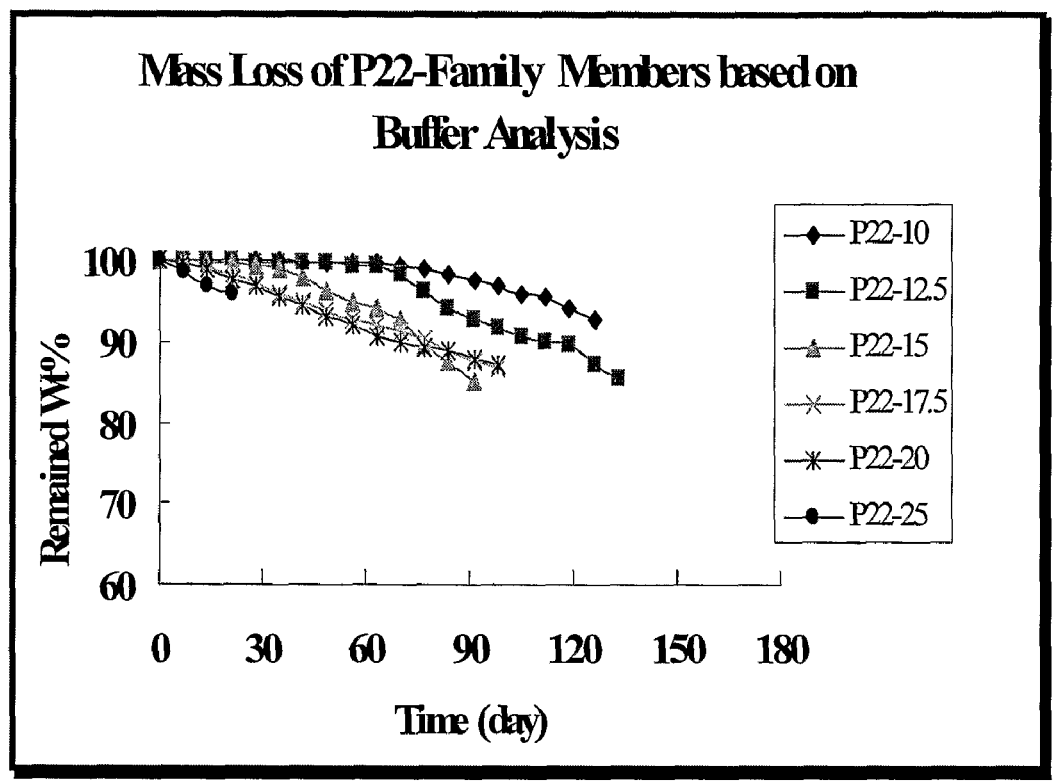
FIG. 2 shows the degradation over time of polymers of the invention.

FIG. 2 shows the mass loss of various members of the DTE succinate family with DT ranging from 10-25% of the diphenol content. The mass loss slows as function of time because the DT is gone.

Figure 3:
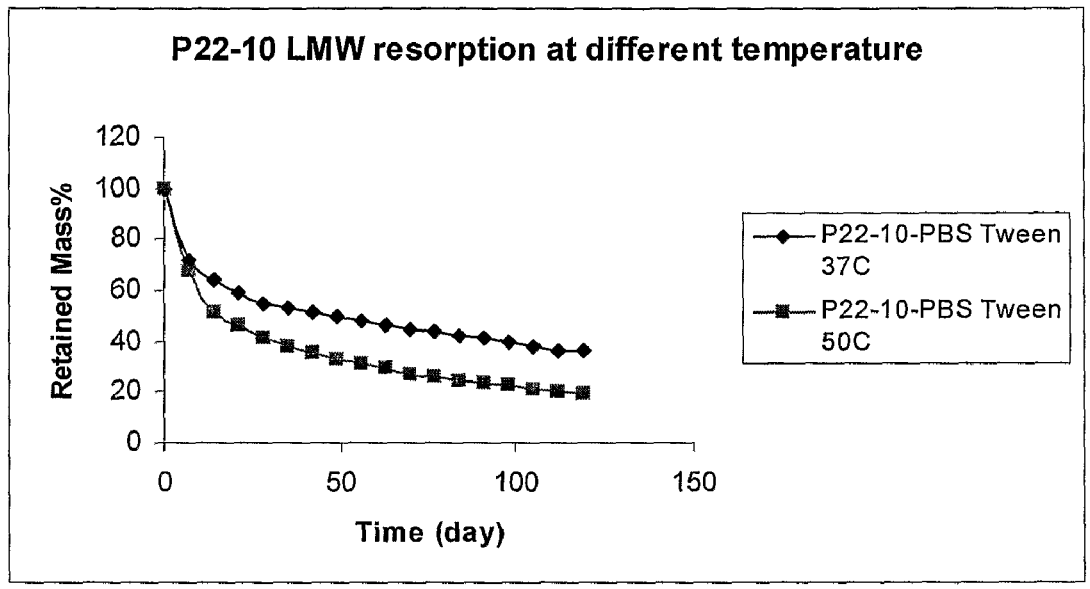
FIG. 3 shows the degradation over time of polymers of the invention.
Figure 4:
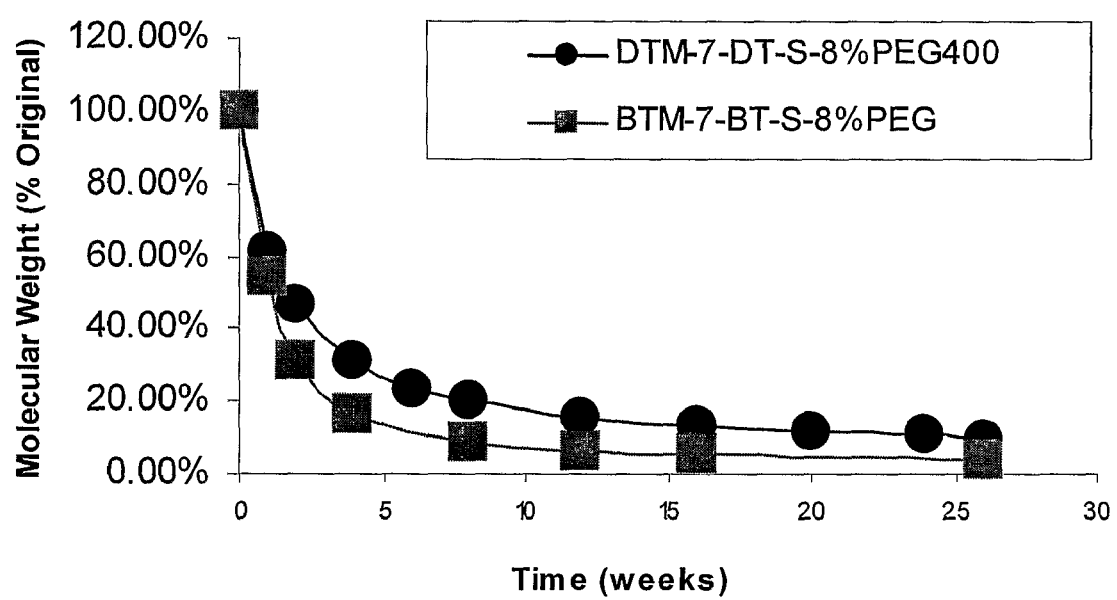
FIG. 4 shows the degradation over time of polymers of the invention.
Figure 5:
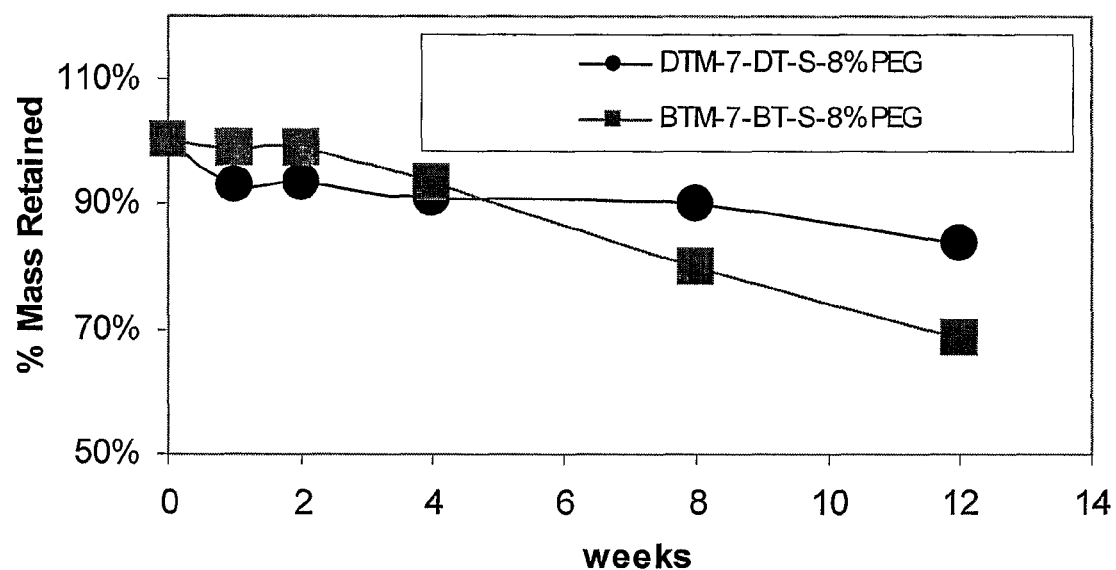
FIG. 5 shows the degradation over time of polymers of the invention.
Figure 6:
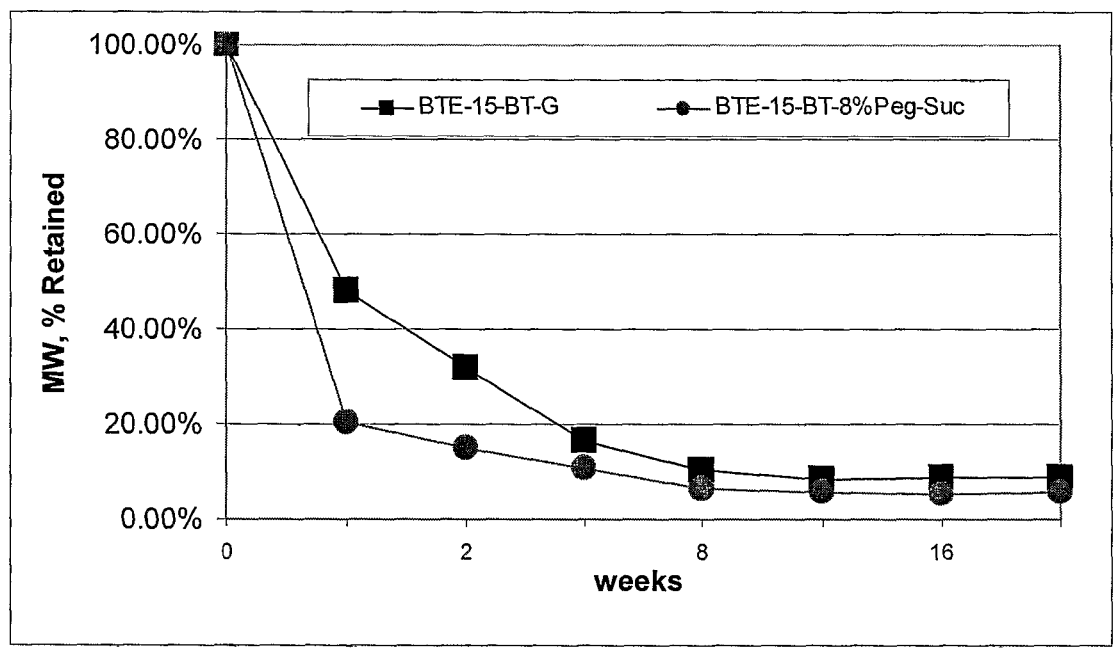
FIG. 6 shows the degradation over time of polymers of the invention.
Figure 7:
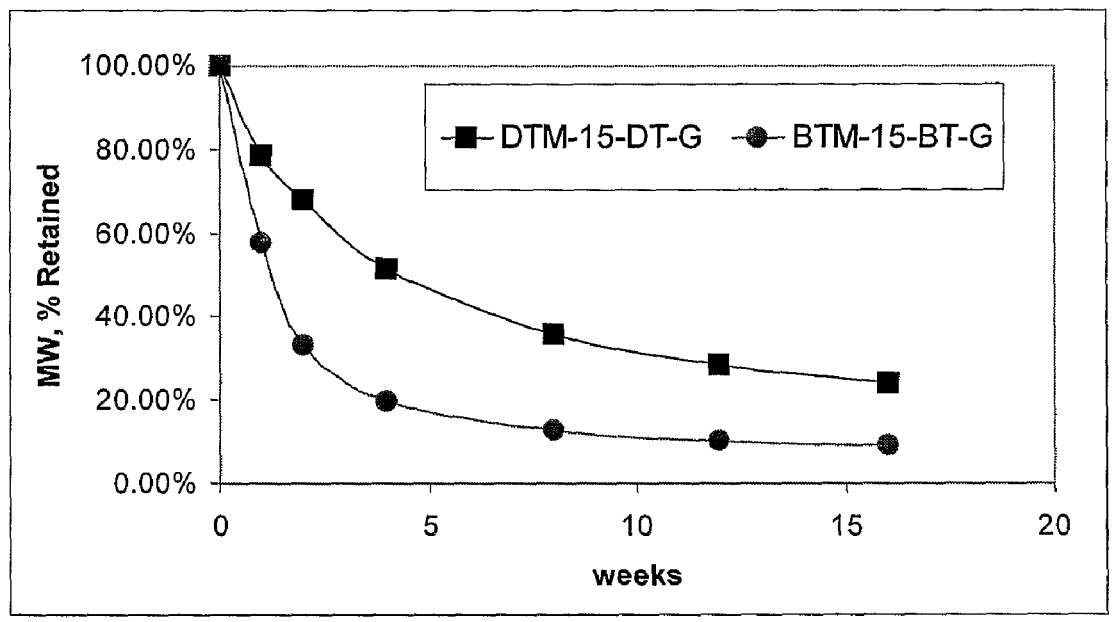
FIG. 7 shows the degradation over time of polymers of the invention.
Figure 8:
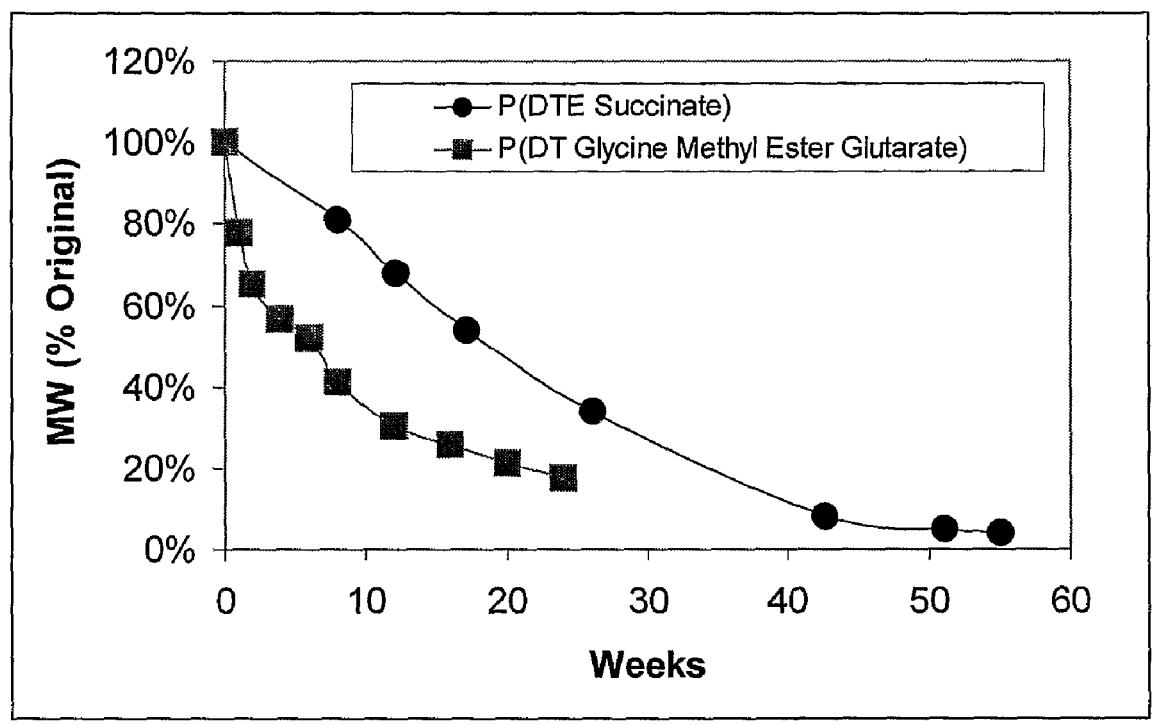
FIG. 8 shows the degradation over time of polymers of the invention.

FIG. 3 shows the mass loss of 10% DT/DTE succinate at 37° C. and 50° C. Mass loss slows down (curve evens out) as all DT is expended from the polymer.

FIGS. 4-8 show the rate of degradation of various polymers of the invention, as measured by the decrease in molecular weight over time.

The table below shows the average molecular weight (MW) and composition of residual fragments of polymers within the DT-DTE succinate family of polymers at various times during in vitro incubation. The residual fragments are analyzed by liquid chromatography-mass spectrometry and relative quantities of peaks for each compound are reported. No indicates that the compound corresponding to that peak was not detectable. The relative total mass is found by the sum of the peak areas for a given compound. From this it is evident that the DT-containing fragments peaks 1 and 4 represent very little of the remaining mass. Peak 8 also contains DT but with twice the amount of DTE-succinate. DTE-suc is DTE-succinate.

Virtually no DT-containing fragments remain at the time points noted and time to total resorption for all of the polymers within the DTE succinate family will be equivalent, because the remaining insoluble fraction in each polymer is chemically equivalent.

| Sample | Peak 1 | Peak 2 | Peak 3 | Peak 4 | Peak 5 | Peak 6 | Peak 7 | Peak 8 | Peak 9 |
|---|---|---|---|---|---|---|---|---|---|
| P22-10 MW = 3000 (6 months) | DT (1.67) | DTE (0.29) | No | DTE-suc-DT (0.68) | No | DTE-suc-DTE (6.1) | DTE-suc-DTE-suc-DT (2.8) | DTE-suc-DTE-suc-DTE (10) | DTE-suc-DTE-suc-DTE (9.5) |
| P22-12.5 MW = 2000 (6 months) | No (0.037) | DTE (2.33) | No | DTE-suc-DT (0.44) | No | DTE-suc-DTE (10) | DTE-suc-DTE-suc-DT (4.5) | DTE-suc-DTE-suc-DTE (8.6) | DTE-suc-DTE-suc-DTE (6.9) |
| P22-15 MW = 3000 (4 months) | DT (0.22) | DTE (0.9) | No | DTE-suc-DT (0.4) | No | DTE-suc-DTE (8.7) | DTE-suc-DTE-suc-DT (2.66) | DTE-suc-DTE-suc-DTE (10) | DTE-suc-DTE-suc-DTE (6.6) |
| P22-17.5 MW = 3700 (3.5 months) | No (0.41) | DTE (0.1) | No | DTE-suc-DT (0.39) | No | DTE-suc-DTE (4.58) | DTE-suc-DTE-suc-DT (2.1) | DTE-suc-DTE-suc-DTE (7.2) | DTE-suc-DTE-suc-DTE (10) |
| P22-20 MW = 3600 (5 months) | DT (0.07) | DTE (0.2) | No | DTE-suc-DT (0.28) | No | DTE-suc-DTE (6.2) | DTE-suc-DTE-suc-DT (1.6) | DTE-suc-DTE-suc-DTE (10) | DTE-suc-DTE-suc-DTE (7.7) |

For P(DTE diglycolate) incubated at 50° C. for 10 days in PBS buffer, the degradation results were as follows:

| Initial MW | MW (avg.) of residual solid at 5 days | MW of residual solid at 10 days |
|---|---|---|
| Solid: 25,000 kD Buffer: none | Solid: 7,000 kD Buffer: DTE | No solid remaining Sample completely resorbed Buffer: DTE |

We claim:

1. A diphenol having structure

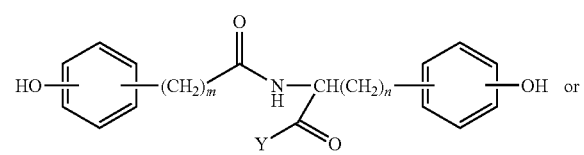

or

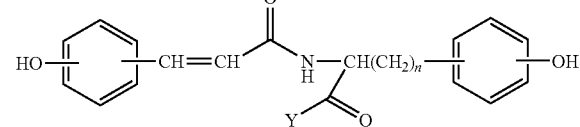

wherein m is 0, 1, or 2; n is 0 to 4, Y is —NHCH$_2$CO$_2$R';

and R' is selected from the group consisting of H, C$_1$-C$_8$ alkyl, C$_2$-C$_8$ alkenyl, C$_8$-C$_{14}$ alkylaryl, benzyl, and substituted benzyl.

2. A polymer consisting essentially of monomer units having the formula

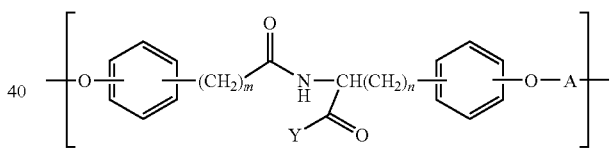

wherein m is 0, 1, or 2; n is 0 to 4, and Y is selected from the group consisting of C$_1$-C$_{18}$ alkylamino, —NHCH$_2$CO$_2$R', —NH(CH$_2$)$_q$OR', —NH(CH$_2$CH$_2$O)$_p$R', —NH(CH$_2$CH$_2$CH$_2$O)$_p$R', where q is 0 to 4, p is 1 to 5000, and R' is selected from the group consisting of H, C$_1$-C$_8$ alkyl, C$_2$-C$_8$ alkenyl, C$_8$-C$_{14}$ alkylaryl, benzyl, and substituted benzyl; and A is selected from the group consisting of —CO—, —C(=NH)—, and —CO—X—CO—, where X is selected from the group consisting of C$_1$-C$_{18}$ alkylene, C$_1$-C$_{18}$ alkenylene, divalent C$_6$-C$_{10}$ arylene, divalent C$_7$-C$_{18}$ alkylaryl, CH$_2$OCH$_2$, CH$_2$—O—(CH$_2$CH$_2$ O)$_s$CH$_2$, (CH$_2$)$_r$CO$_2$(CH$_2$CH$_2$CH$_2$O)$_s$CO(CH$_2$)$_r$, and (CH$_2$)$_r$CO$_2$(CH$_2$CH$_2$O)$_s$CO(CH$_2$)$_r$, where r is 2 to 4 and s is 1 to 5000.

3. A polymer consisting essentially of monomer units having the formula

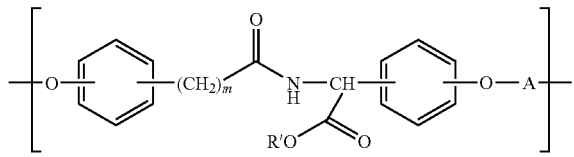

wherein m is 0, 1, or 2; R' is selected from the group consisting of H, C$_1$-C$_{18}$ alkyl, C$_2$-C$_{18}$ alkenyl, C$_8$-C$_{18}$ alkylaryl, benzyl, and substituted benzyl; and A is selected from the group consisting of —CO—, —C(=NH)—, and —CO—X—CO—, where X is selected from the group consisting of C$_1$-C$_{18}$ alkylene, C$_1$-C$_{18}$ alkenylene, divalent C$_6$-C$_{10}$ arylene, divalent C$_7$-C$_{18}$ alkylaryl, CH$_2$OCH$_2$, CH$_2$—O—(CH$_2$CH$_2$O)$_s$CH$_2$, (CH$_2$)$_r$CO$_2$(CH$_2$CH$_2$CH$_2$O)$_s$CO(CH$_2$)$_r$, and (CH$_2$)$_r$CO$_2$(CH$_2$CH$_2$O)$_s$CO(CH$_2$)$_r$, where r is 2 to 4 and s is 1 to 5000.

4. A polymer according to claim 2, wherein A is —CO—X—CO—.

5. A polymer according to claim 2, wherein between 0.1% and 99.9% of the X moieties are (CH$_2$)$_r$CO$_2$(CH$_2$CH$_2$O)$_s$CO(CH$_2$)$_r$ or (CH$_2$)$_r$CO$_2$(CH$_2$CH$_2$CH$_2$O)$_s$CO(CH$_2$)$_r$.

6. A polymer comprising monomer units having formula

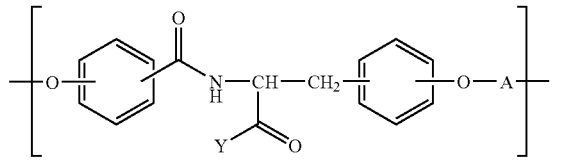

wherein Y is OMe or OEt, A is selected from the group consisting of —CO—, —C(=NH)—, and —CO—X—CO—, and X is selected from the group consisting of CH$_2$CH$_2$, CH$_2$CH$_2$CH$_2$, and CH$_2$—O—(CH$_2$CH$_2$O)$_s$CH$_2$, and s is 0 to 200.

7. A polymer according to claim 6, further comprising monomer units independently having formula

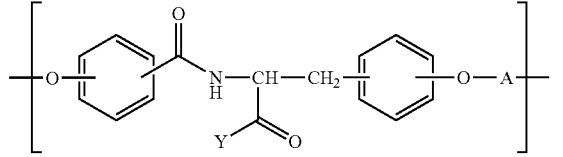

wherein Y is OH or O-benzyl and A is selected from the group consisting of —CO—, —C(=NH)—, and —CO—X—CO—, and X is selected from the group consisting of CH$_2$CH$_2$, CH$_2$CH$_2$CH$_2$, and CH$_2$—O—(CH$_2$CH$_2$O)$_s$CH$_2$, and s is 0 to 200.

8. A polymer comprising monomer units having the formula

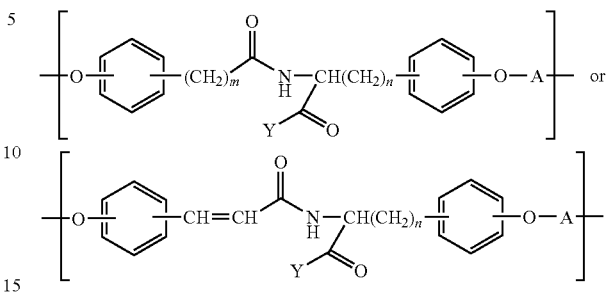

wherein m is 0, 1, or 2; n is 0 to 4, Y is —NHCH$_2$CO$_2$R'; and R' is selected from the group consisting of H, C$_1$-C$_8$ alkyl, C$_2$-C$_8$ alkenyl, C$_8$-C$_{14}$ alkylaryl, benzyl, and substituted benzyl; and A is selected from the group consisting of —CO—, —C(=NH)—, and —CO—X—CO—, where X is selected from the group consisting of C$_1$-C$_{18}$ alkylene, C$_1$-C$_{18}$ alkenylene, divalent C$_6$-C$_{10}$ arylene, divalent C$_7$-C$_{18}$ alkylaryl, CH$_2$OCH$_2$, CH$_2$—O—(CH$_2$CH$_2$O)$_s$CH$_2$, (CH$_2$)$_r$CO$_2$(CH$_2$CH$_2$CH$_2$O)CO$_s$(CH$_2$)$_r$, and (CH$_2$)$_r$CO$_2$(CH$_2$CH$_2$O)$_s$CO(CH$_2$)$_r$, where r is 2 to 4 and s is 1 to 5000.

9. A polymer comprising monomer units having the formula

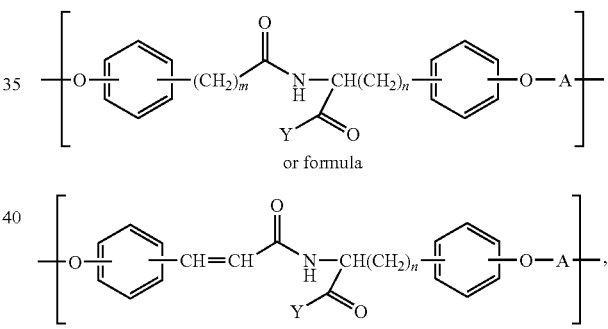

wherein m is 0, 1, or 2; n is 0 to 4, and Y is selected from the group consisting of C$_1$-C$_{18}$ alkylamino, —NHCH$_2$CO$_2$R', —NH(CH$_2$)$_q$OR', —NH(CH$_2$CH$_2$O)$_p$R', —NH(CH$_2$CH$_2$CH$_2$O)$_p$R',

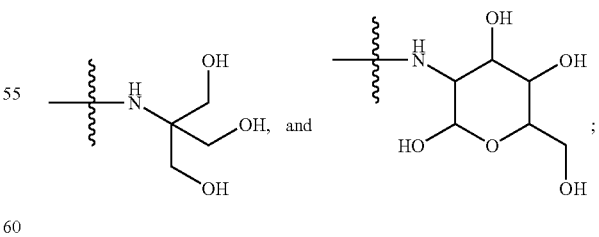

where q is 0 to 4, p is 1 to 5000, and R' is selected from the group consisting of H, C$_1$-C$_8$ alkyl, C$_2$-C$_8$ alkenyl, C$_8$-C$_{14}$ alkylaryl, benzyl, and substituted benzyl; and A is —CO—X—CO—, where X is selected from the group consisting of C$_1$-C$_{18}$ alkylene, C$_1$-C$_{18}$ alkenylene, divalent C$_6$-C$_{10}$ arylene, divalent C$_7$-C$_{18}$ alkylaryl, CH$_2$OCH$_2$, CH$_2$—O—(CH$_2$CH$_2$O)$_s$CH$_2$, (CH$_2$)$_r$CO$_2$ $(CH_2CH_2CH_2O)_sCO(CH_2)_r$, and $(CH_2)_rCO_2(CH_2CH_2O)_sCO(CH_2)_r$, where r is 2 to 4 and s is 1 to 5000.

10. A polymer comprising monomer units having the formula

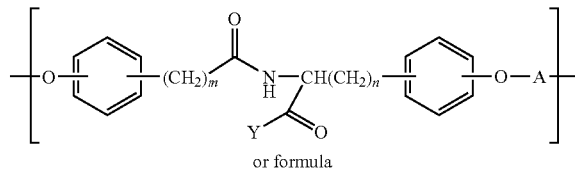

or formula

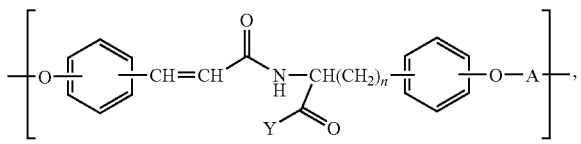

wherein m is 0, 1, or 2; n is 0 to 4, and Y is selected from the group consisting of $C_1$-$C_{18}$ alkylamino, —$NHCH_2CO_2R'$, —$NH(CH_2)_qOR'$, —$NH(CH_2CH_2O)_pR'$, —$NH(CH_2CH_2CH_2O)_pR'$,

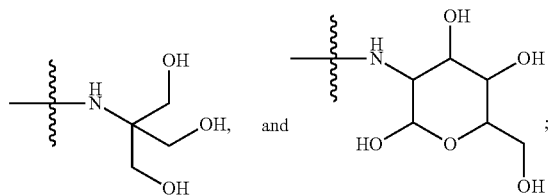

where q is 0 to 4, p is 1 to 5000, and R' is selected from the group consisting of H, $C_1$-$C_8$ alkyl, $C_2$-$C_8$ alkenyl, $C_8$-$C_{14}$ alkylaryl, benzyl, and substituted benzyl; and A is selected from the group consisting of —CO—, —C(=NH)—, and —CO—X—CO—, where X is selected from the group consisting of $C_1$-$C_{18}$ alkylene, $C_1$-$C_{18}$ alkenylene, divalent $C_6$-$C_{10}$ arylene, divalent $C_7$-$C_{18}$ alkylaryl, $CH_2OCH_2$, $CH_2$—O—$(CH_2CH_2O)_sCH_2$, $(CH_2)_rCO_2(CH_2CH_2O)_sCO(CH_2)_r$, and $(CH_2)_rCO_2(CH_2CH_2O)_sCO(CH_2)_r$, where r is 2 to 4 and s is 1 to 5000, wherein between 0.1% and 99.9% of the X moieties are $(CH_2)_rCO_2(CH_2CH_2O)_sCO(CH_2)_r$ or $(CH_2)_rCO_2(CH_2CH_2CH_2O)_sCO(CH_2)_r$.

11. A polymer according to claim 9, wherein between 0.1% and 99.9% of the X moieties are $(CH_2)_rCO_2(CH_2CH_2O)_sCO(CH_2)_r$ or $(CH_2)_rCO_2(CH_2CH_2CH_2O)_sCO(CH_2)_r$.

12. The polymer according to claim 10, wherein A is —CO—X—CO—.

13. A polymer according to any one of claims 8, 9, or 10 further comprising monomer units independently having the formula

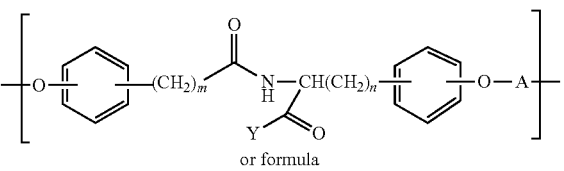

or formula

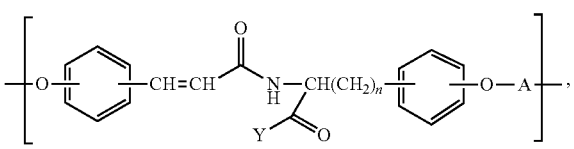

wherein m is 0, 1, or 2; n is 0 to 4; A is selected from the group consisting of —CO—, —C(=NH)—, and —CO—X—CO—, where X is selected from the group consisting of $C_1$-$C_{18}$ alkylene, $C_1$-$C_{18}$ alkenylene, divalent $C_6$-$C_{10}$ arylene, divalent $C_7$-$C_{18}$ alkylaryl, $CH_2OCH_2$, $CH_2$—O—$(CH_2CH_2O)_sCH_2$, $(CH_2)_rCO_2(CH_2CH_2CH_2O)_sCO(CH_2)_r$, and $(CH_2)_rCO_2(CH_2CH_2O)_sCO(CH_2)_r$, where r is 2 to 4 and s is 1 to 5000; and Y is OH or O-benzyl.

14. A polymer according to claim 13, wherein between 1% and 50% of the monomer units have formula

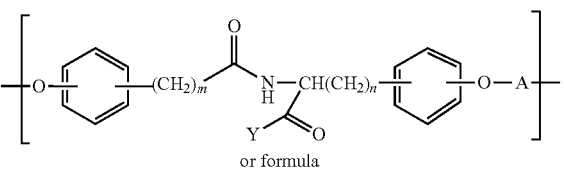

or formula

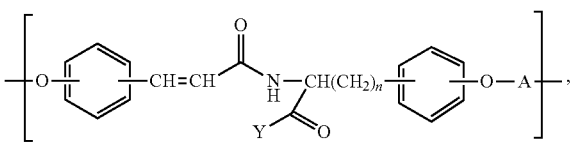

wherein Y is OH or O-benzyl.

* * * * *